US012788231B2

(12) United States Patent
Lim

(10) Patent No.: US 12,788,231 B2
(45) Date of Patent: Nov. 10, 2026

(54) SINGLE PIECE ARTICULATING LINKS WITH ON-AXIS BEVEL HINGE CUT

(71) Applicant: Boston Scientific Scimed, Inc., Maple Grove, MN (US)

(72) Inventor: Kian S. Lim, Shrewsbury, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 198 days.

(21) Appl. No.: 18/438,726

(22) Filed: Feb. 12, 2024

(65) Prior Publication Data

US 2024/0268642 A1 Aug. 15, 2024

Related U.S. Application Data

(60) Provisional application No. 63/484,840, filed on Feb. 14, 2023.

(51) Int. Cl.
*A61B 1/008* (2006.01)

(52) U.S. Cl.
CPC .................................... *A61B 1/008* (2013.01)

(58) Field of Classification Search
CPC ...... A61B 1/005; A61B 1/008; B23K 15/002; B23K 15/0006; B23K 15/0013
See application file for complete search history.

(56) References Cited

U.S. PATENT DOCUMENTS

| | | | | |
|---|---|---|---|---|
| 5,249,818 A * | 10/1993 | Patterson | ........... | B23K 26/0823 280/281.1 |
| 12,048,819 B2 * | 7/2024 | Yang | ................. | A61M 25/0013 |
| 2017/0156567 A1 | 6/2017 | Kaneko et al. | | |
| 2023/0016068 A1 | 1/2023 | Sato et al. | | |

FOREIGN PATENT DOCUMENTS

| | | | |
|---|---|---|---|
| CN | 107334449 A * | 11/2017 | ............. A61B 1/008 |
| CN | 111110172 A * | 5/2020 | ........... A61B 1/0055 |
| CN | 116831504 A * | 10/2023 | ........... A61B 1/0055 |
| DE | 4317914 A1 * | 12/1994 | ......... G02B 23/2476 |

(Continued)

OTHER PUBLICATIONS

CN-107334449-A (Year: 2017).*

(Continued)

*Primary Examiner* — Jason L Vaughan
(74) *Attorney, Agent, or Firm* — Bookoff McAndrews, PLLC

(57) ABSTRACT

A medical device includes an articulating joint cut from a tubular member to include a plurality of links. Each of the links extends from a proximal end to a distal end and including a channel extending therethrough. The proximal end of each of the plurality of links includes a proximal engaging feature and the distal end of each of the plurality of links including a distal engaging feature. The proximal engaging feature of one of the links is configured to movably engage the distal engaging feature of an adjacent one of the links to form a hinge via which adjacent links are movable relative to one another and the articulating joint is movable between a straight configuration and a bent configuration. The proximal and distal engaging features include partial bevels corresponding to one another and extending therealong.

5 Claims, 5 Drawing Sheets

(56) References Cited

FOREIGN PATENT DOCUMENTS

| | | | | | |
|---|---|---|---|---|---|
| DE | 102016118158 | B3 | * | 1/2018 | ............. A61B 17/29 |
| GB | 2602024 | A | * | 6/2022 | ............... A61B 1/01 |
| JP | H09117413 | A | * | 5/1997 | ........... A61B 1/0055 |
| WO | WO-2022148280 | A1 | * | 7/2022 | ........... A61B 1/0055 |

OTHER PUBLICATIONS

CN-111110172-A (Year: 2020).*
CN-116831504-A (Year: 2023).*
DE-102016118158-B3 (Year: 2006).*
DE-10202218473-A1 (Year: 2018).*
DE-4317914-A1 (Year: 1994).*
GB-2602024-A (Year: 2020).*
JP-H09117413-A (Year: 1997).*
WO-2022148280-A1 (Year: 2022).*
International Search Report and Written Opinion in International Application No. PCT/US2024/015317, dated May 3, 2024 (11 pages).

* cited by examiner

SINGLE PIECE ARTICULATING LINKS WITH ON-AXIS BEVEL HINGE CUT

CROSS-REFERENCE TO RELATED APPLICATIONS

This application claims the benefit of priority to U.S. Provisional Application No. 63/484,840, filed on Feb. 14, 2023, which is incorporated by reference herein in its entirety.

BACKGROUND

Many scope devices (e.g., endoscopes, ureteroscopes) and/or other medical devices are inserted through tortuous paths of a body lumen and may thus include an articulating joint along, for example, at a distal portion of a shaft thereof, for facilitating navigation of the scope or medical device through the body lumen. The articulating joint may be formed of a plurality of links movably connected to one another so that the distal portion of the shaft is bendable therealong to deflect a distal end of the shaft relative to a longitudinal axis of the shaft. In some cases, an articulating joint can include 20 or more links to achieve a desired bending radius. A conventional articulating joint may be cut (e.g., laser cut) from a tubular body using, e.g., a 5-axis laser cutter, which utilizes a revolving laser and a mirror to cut each of the links. Angled cuts are achieved by using the mirror to reflect a laser beam. 5-axis laser cutters, however, are costly, limited in angulations of cuts, are often not accurate enough to achieve a desired tolerance, and it may be difficult to maintain consistent dimensions for all of the links.

SUMMARY

The present disclosure relates to a medical device which includes an articulating joint cut (e.g., laser cut) from a tubular member to include a plurality of links. Each of the links extends from a proximal end to a distal end and includes a channel extending therethrough. The proximal end of each of the plurality of links includes a proximal engaging feature and the distal end of each of the plurality of links includes a distal engaging feature. The proximal engaging feature of one of the links is configured to movably engage the distal engaging feature of an adjacent one of the links to form a hinge via which adjacent links are movable relative to one another and the articulating joint is movable between a straight configuration and a bent configuration. The proximal and distal engaging features include partial bevels corresponding to one another and extending therealong.

In an embodiment, the proximal and distal engaging features includes a pair of rounded tabs extending from diametrically opposing portions of a corresponding one of a proximal edge and a distal edge of each of the plurality of links.

In an embodiment, another one of the proximal and distal engaging features includes a pair of rounded indentations sized and shaped to correspond to the rounded tabs so that the rounded tabs of an adjacent link are rotatably received therein, the indentations extending through a wall of each of the plurality of links along a corresponding one of the proximal and distal edges thereof.

In an embodiment, a portion of an edge midway along a periphery of each of the rounded tabs extends substantially perpendicular to an exterior surface of each link and portions of the edge along opposing sides of each of the rounded tabs include the partial bevel.

In an embodiment, a midpoint of an edge defining each of the indentations is substantially perpendicular to an exterior surface of each link and portions of the edge along opposing sides of each of the indentations are beveled to correspond to the partial bevel of the rounded tabs.

In an embodiment, the rounded tabs of a first one of the links is received within the indentations of a second one of the links so that the rounded tabs are rotatable therewithin about an axis extending through center points of the indentations.

In an embodiment, the proximal edge of each of the links tapers toward the proximal engaging feature and the distal edge of each of the links tapers toward the distal engaging feature so that there is sufficient space between adjacent links for the adjacent links to be rotated relative to one another.

In an embodiment, the articulating joint is symmetrical about a plane along which the articulating joint is configured to be moved between the straight configuration and the bent configuration.

In addition, the present disclosure relates to a system for laser cutting an articulating joint. The system includes a non-transitory computer-readable storage medium storing an executable program and a processor executing the executable program to cause the processor to do the following: control a laser to be movable along three axes and to rotate a tubular member about a longitudinal axis corresponding to one of the three axes so that the articulating joint is cut therefrom via the laser, the articulating joint including a plurality of links, each of the links extending from a proximal end to a distal end, the proximal end of each of the plurality of links including a proximal engaging feature and the distal end of each of the plurality of links including a distal engaging feature, the proximal engaging feature of one of the links configured to movably engage the distal engaging feature of an adjacent one of the links to form a hinge via which adjacent links are rotatable relative to one another and the articulating joint is movable between a straight configuration and a bent configuration, the laser cutting the tubular member so that the proximal and distal engaging features including partial bevels corresponding to one another and extending therealong to prevent adjacent links from separating from one another.

In an embodiment, the processor controls the laser to cut the tubular member to define the hinge between adjacent links, one of the proximal and distal engaging features including a pair of rounded tabs extending from diametrically opposing portions of a corresponding one of a proximal edge and a distal edge of each of the plurality of links and another one of the proximal and distal engaging features including a correspondingly sized and shaped pair of rounded indentations extending through a wall of each of the plurality of links along a corresponding one of the proximal and distal edges thereof.

In an embodiment, the processor controls the laser to cut the hinge so that the rounded tabs of a first one of the links is configured to be rotated within the corresponding indentations of a second, adjacent one of the links about an axis extending through center points of the indentations.

In an embodiment, the processor controls the laser to extend perpendicular relative to the longitudinal axis along a portion of the tubular member to form a corresponding straight edge along a portion of the rounded tabs and a portion of the indentations.

In an embodiment, the processor controls the laser to cut a corresponding bevel along opposing sides of the rounded tabs and the indentations, an angle of the bevel determined via a distance of the laser from a longitudinal axis of the tubular member and a rotation of the tubular member.

In an embodiment, the processor controls the laser to cut out portions of the tubular member to define the proximal and distal edges of each of the links, the proximal edge of each of the links tapering toward the proximal engaging feature and the distal edge of each of the links tapering toward the distal engaging feature so that there is sufficient space between adjacent links for the adjacent links to be rotated relative to one another.

In an embodiment, the processor controls the laser to cut the tubular member so that the articulating joint is symmetrical about a plane along which the articulating joint is configured to be moved between the straight configuration and the bent configuration.

In addition, the present disclosure relates to a method for manufacturing an articulating joint of a medical device. The method includes laser cutting a tubular member to form the articulating joint including a plurality of links using a four-axis laser cutter including a laser movable along three axes and the tubular member rotatable about a longitudinal axis thereof. Each of the links extends from a proximal end to a distal end. The proximal end of each of the plurality of links includes a proximal engaging feature and the distal end of each of the plurality of links including a distal engaging feature. The proximal engaging feature of one of the links is configured to movably engage the distal engaging feature of an adjacent one of the links to form a hinge via which adjacent links are rotatable relative to one another and the articulating joint is movable between a straight configuration and a bent configuration. The proximal and distal engaging features includes partial bevels corresponding to one another and extending therealong to prevent adjacent links from separating from one another.

In an embodiment, the laser cuts the tubular member to define the hinge between adjacent links, one of the proximal and distal engaging features including a pair of rounded tabs extending from diametrically opposing portions of a corresponding one of a proximal edge and a distal edge of each of the plurality of links and another one of the proximal and distal engaging features including a correspondingly sized and shaped pair of rounded indentations extending through a wall of each of the plurality of links along a corresponding one of the proximal and distal edges thereof.

In an embodiment the laser extends perpendicular relative to the longitudinal axis along a portion of the tubular member to cut a straight edge along corresponding portions of the proximal and distal engaging features.

In an embodiment the laser cuts a bevel along opposing sides of the rounded tabs and the indentations, an angle of the bevel determined via a distance of the laser from a longitudinal axis of the tubular member and a rotation of the tubular member.

In an embodiment the laser cuts out portions of the tubular member to define the proximal and distal edges of each of the links so that the proximal edge of each of the links tapers toward the proximal engaging feature and the distal edge of each of the links tapers toward the distal engaging feature so that there is sufficient space between adjacent links for the adjacent links to be rotated relative to one another.

DETAILED DESCRIPTION

Figure 1:
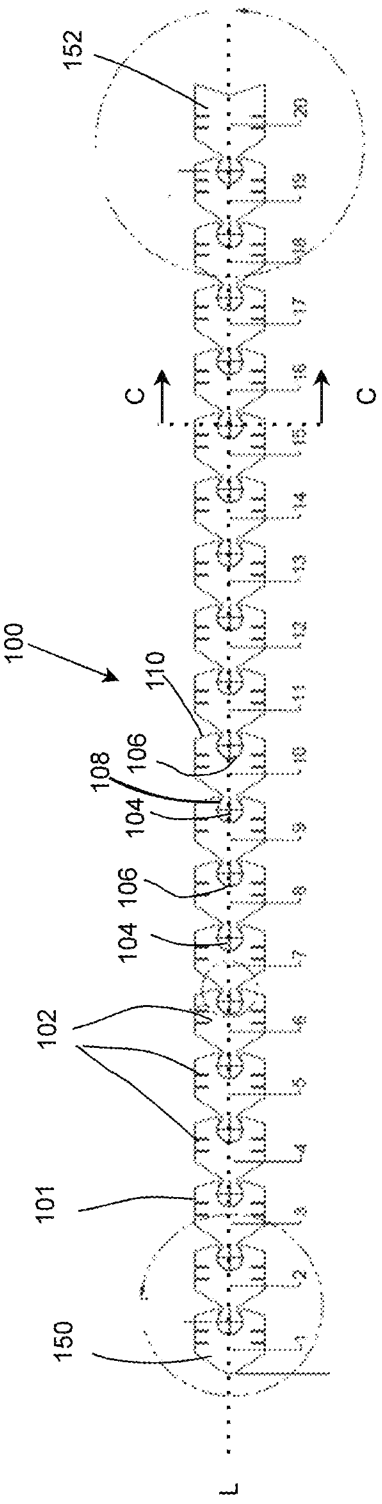
FIG. 1 shows a longitudinal side view of an articulating joint cut from a single, tubular member according to an exemplary embodiment of the present disclosure.

The present disclosure may be further understood with reference to the following description and appended drawings, wherein like elements are referred to with the same reference numerals. The present disclosure relates to a medical device and, in particular, relates to a medical device including an articulating joint. Exemplary embodiments of the present disclosure describe an articulating joint configured to extend along, for example, a distal portion of a shaft of a medical device such as an endoscope or ureteroscope. The exemplary articulating joint may be formed from a single tubular member that is cut (e.g., laser cut) to form a plurality of links with each of the links connected to one or two adjacent links via corresponding mating features which engage one another to form a hinge that allows the adjacent links to be rotated relative to one another.

According to an exemplary embodiment, the tubular member is cuttable via a 4-axis laser cutter (i.e., a device including a laser movable along three axes (e.g., X, Y, and Z axes)) while the tubular member is rotated about its longitudinal axis. The laser cutter laser cuts the tubular member to define each of the links and, in particular, cuts a portion of the hinge to include a partial bevel that prevents adjacent links from separating from one another. Although the exemplary embodiments describe the articulating joint as configured for scope devices including, for example, endoscopes and ureteroscopes, it will be understood by those of skill in the art that the articulating joint may be utilized in any of variety of medical devices in which bending along any portion of a shaft thereof is desired. It will also be understood by those of skill in the art that the terms "proximal" and "distal," as used herein, are intended to refer to a direction toward (proximal) and away from (distal) a user of the device (e.g., physician).

As shown in FIGS. 1-8, an articulating joint 100 according to an exemplary embodiment of the present disclosure comprises a plurality of links 102 movably connected to one another to facilitate bending of the articulating joint 100 within a plane including a longitudinal axis L of the articulating joint 100. As would be understood by those skilled in the art, the term axis as used herein describes a path along the center of the articulating joint 100 from the proximal end of the articulating joint 100 to its distal end. This axis may be curved or straight depending on the disposition of the articulating joint 100 at a given time and, within certain tolerances, the axis may deviate from a plane. However, the articulating joint 100 of this embodiment is formed so that, the bending of the articulating joint 100 along the axis is substantially within a single plane.

As shown in FIG. 1, the articulating joint 100 of this embodiment is cut from a single, tubular member 101, which extends along the longitudinal axis L from a proximal end 150 to a distal end 152 and is configured to form, for example, a distal portion of a shaft of a medical device (e.g., endoscope, ureteroscope) to enhance the bending of the shaft in this portion so that a user (e.g., a physician) may steer a distal end of the shaft to navigate the shaft through tortuous paths of a body lumen. As would be understood by those skilled in the art, an articulating joint according to a further embodiment, may be constructed in the same manner as the articulating joint 100 except that the proximal and distal ends in the further embodiment are reversed in comparison to the articulating joint 100. That is, the joint of the further embodiment, may be structured in the same manner as the articulating joint 100 except that the proximal end of the further joint would be at the end of the articulating joint 100 indicated by 152 while the distal end of the joint of the further embodiment would be at the end indicated by 150.

Figure 3:
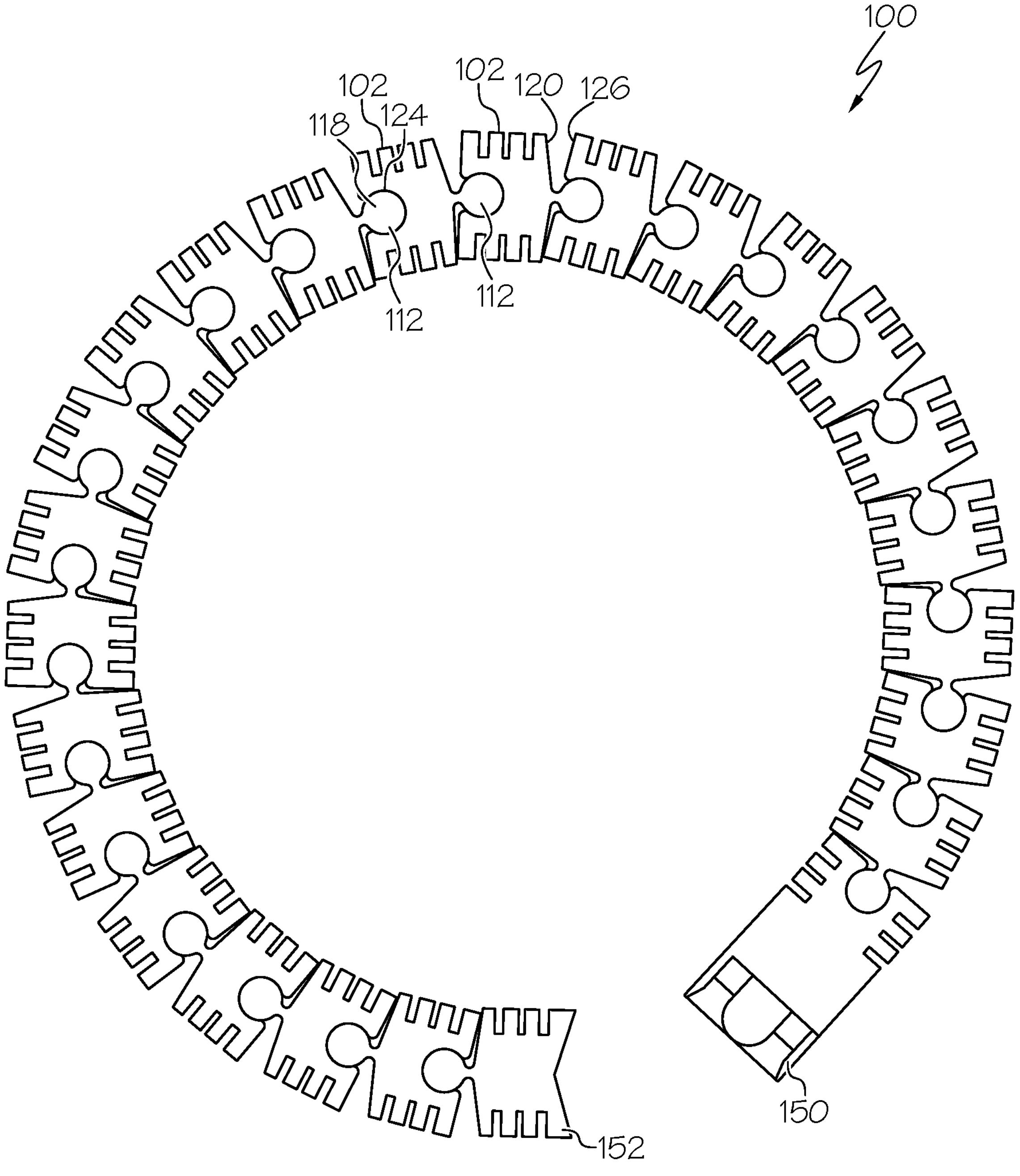
FIG. 3 shows a longitudinal side view of the articulating joint of FIG. 1, in a bent configuration.

Each of the links 102 of the articulating joint 100 includes a proximal engaging feature 104 at a proximal end 108 thereof and a distal engaging feature 106 at a distal end 110 thereof. Each of the proximal engaging features 104 corresponds in size and shape to the distal engaging feature 106 with which it is engaged so that the proximal engaging feature 104 of a first link 102*a* engages the distal engaging feature 106 of a second link 102*b* adjacent to the first link 102*a* to form a hinge 112 therebetween. The hinge 112 is configured to permit the adjacent links 102*a*, 102*b* to be moved (e.g., rotated) relative to one another. The hinge 112 facilitates rotation of each of the adjacent links 102*a*, 102*b* relative to one another so that the articulating joint 100 may be moved to any position between a substantially straight configuration, as shown in FIG. 1, and a fully bent configuration, as shown in FIG. 3. As will be described in further detail below, to prevent the adjacent links 102*a*, 102*b* from separating from one another at the hinge 112, an angled cut 114 is formed in the tubular member 101 of this embodiment to define proximal and distal engaging features 104, 106 of the adjacent links 102*a*, 102*b* with corresponding partial bevels 128, 138, respectively.

Figure 2:
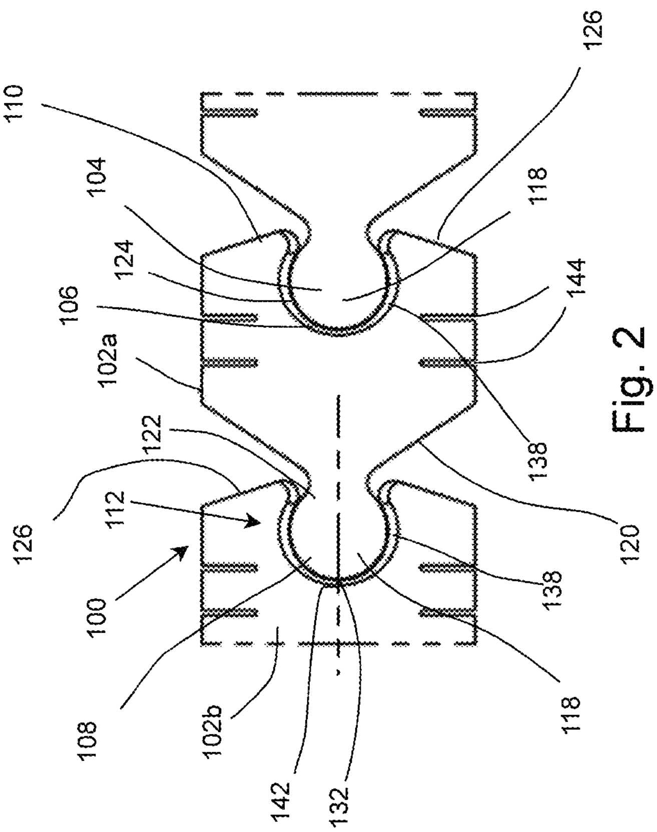
FIG. 2 shows an enlarged longitudinal side view of adjacent links of the articulating member according to FIG. 1, connected to one another via a hinge.
Figure 4:
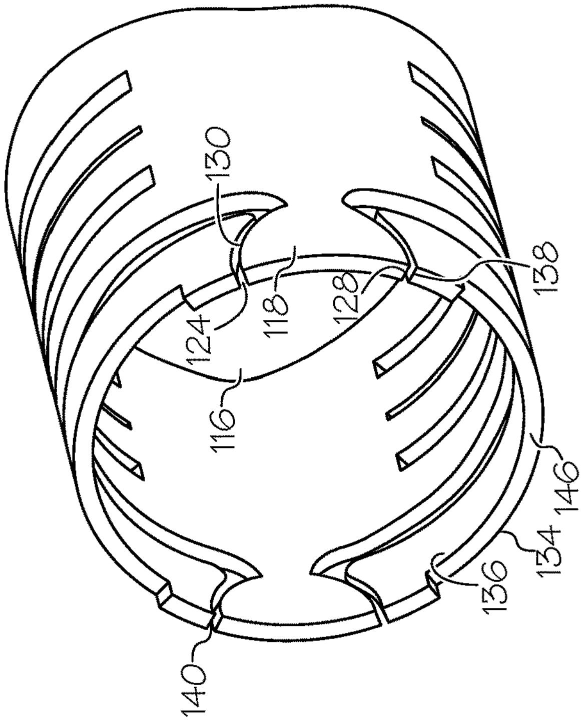
FIG. 4 shows a perspective cross sectional view of a portion of the articulating joint along line C-C, according to FIG. 1.

As described above, the articulating joint 100 comprises the links 102 each of which, as shown in FIGS. 2 and 4, extends from the proximal end 108 to the distal end 110 and includes a channel 116 extending therethrough. The proximal engaging feature 104 of each of the links 102 defines a proximal edge 120 forming a proximal-facing end surface of each of the links 102. In an exemplary embodiment, the proximal engaging feature is configured as a pair of rounded tabs 118 extending proximally from the proximal edge 120 along diametrically opposed portions of the link 102. In particular, the proximal edge 120 extends between and connects a radially exterior surface 134 (i.e., a surface furthest from and facing away from the axis L) and an interior surface 136 of the link 102 (facing the axis L). In an exemplary embodiment, each of the rounded tabs 118 is substantially circular. Portions of the proximal edge 120 on either side of each of the rounded tabs 118 is angled to taper toward a distal end 122 of each of the rounded tabs 118 until each of the tapered edges extending away from a first one of the rounded tabs 118 meets a corresponding one of the edges extending away from the second one of the rounded tabs 118.

Similarly, the distal end 110 of each of the links 102 includes the distal engaging feature 106 forming a distal edge 126 of each of the links 102. In this embodiment, each of the distal engaging features 106 includes a pair of diametrically opposed indentations 124 extending through a wall 146 of one of the links 102 (e.g., the second link 102*b*), from the exterior surface 134 to the interior surface 136. Each of the indentations 124 of the second link 102*b* is configured (sized, shaped, and positioned) to rotatably receive a corresponding one of the rounded tabs 118 of the adjacent immediately more distal first link 102*a*. The distal edge 126 of the second link 102*b* extends between the exterior and interior surfaces 134, 136 of the second link 102*b* to connect the exterior and interior surfaces 134, 136 at the distal end 110 of the second link 102*b*.

As indicated above, the indentations 124 of the second link 102*b* are sized and shaped to correspond to the rounded tabs 118 of the first link 102*a* and extend from the distal edge 126, through diametrically opposed portions of the second link 102*b*, in longitudinal alignment with the rounded tabs 118 of the first link 102*a*. In an exemplary embodiment, each of the indentations 124 of the second link 102*b* is substantially circular to match the circular shape of the rounded tabs 118 of the first link 102*a* so that these rounded tabs 118 and the corresponding indentations 124 act as a hinge 112 between the first and second links 102*a*, 102*b*. This hinge 112 permits rotation of the adjacent first and second links 102*a*, 102*b* relative to one another, about an axis extending through, for example, a center point of each of the indentations 124. The distal edge 126 is also angled to taper toward the distal end 110 so that, the angle of the proximal and distal edges 120, 126 provide sufficient clearance between the adjacent links 102*a*, 102*b* as the adjacent links 102*a*, 102*b* are rotated relative to one another. Those skilled in the art will understand that this same relation between the indentations 124 of any of the links 102 and the rounded tabs 118 of the second link 102*b* immediately distal thereto will be similar so long as the size, shape and position of the rounded tabs 118 and the indentation 124 of each pair of adjacent links 102 are selected to permit mechanical engagement maintaining a coupling between the links 102 while permitting rotation relative to one another through a permitted range of rotation.

As will be described in further detail below, according to an exemplary embodiment, the articulating joint 100 is cut from a single tubular member 101 formed of, for example, a metal. The tubular member 101 may be cut using, e.g., a laser cutter to define each of the individual links 102. To prevent the adjacent links 102 from being separated from one another, a portion of each hinge 112 of this embodiment is cut at an angle so that each of the rounded tabs 118 and the indentations 124 includes a partial bevel 128, 138, respectively, which correspond to one another to permit mating therebetween.

Figure 5:
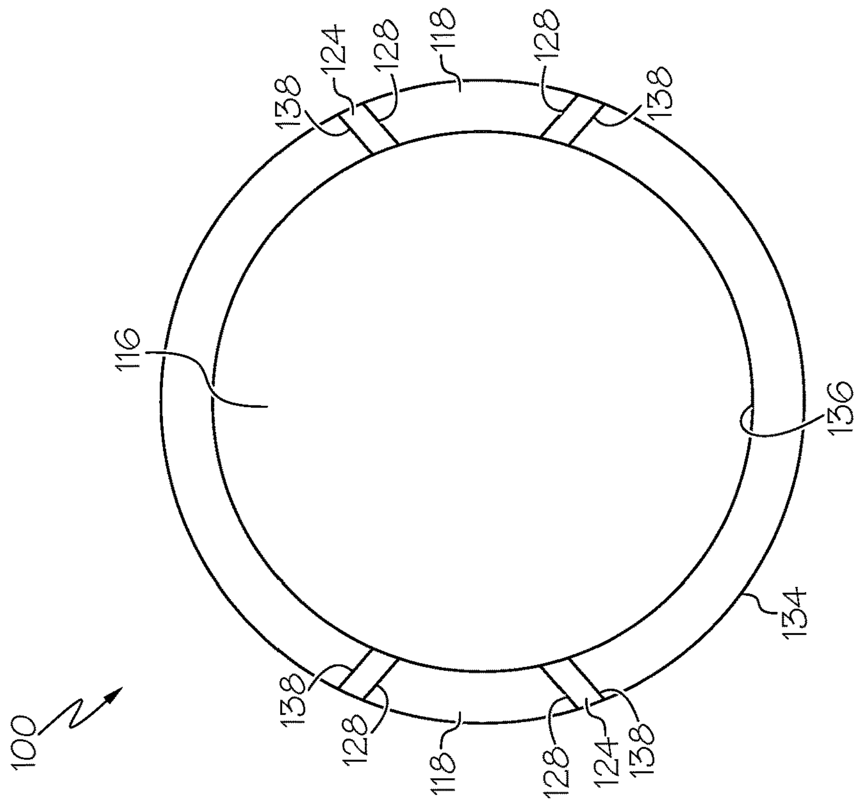
FIG. 5 shows a cross-sectional plan view of the articulating joint along line C-C, according to FIG. 1.

In an exemplary embodiment, a proximal-most point 132 of each of the rounded tabs 118 includes a straight edge. In other words, an edge 130 of each of the rounded tabs 118 at the proximal-most point 132 (e.g., a midpoint along a periphery of the rounded tab 118) thereof extends substantially perpendicular to the interior and exterior surfaces 136, 134 of the rounded tab 118—e.g., perpendicular to the exterior surface 134 and/or the interior surface 136 of the link 102 of the tubular member 101. The bevel 128, however, extends along portions of the edge 130 of each of the rounded tabs 118 extending between the proximal-most point 132 and the distal end 122 thereof, along opposing sides of the rounded tabs 118, as shown in FIGS. 4 and 5. The bevel 128 extends at a non-perpendicular angle relative to the exterior and interior surfaces 134, 136 of each of the links 102.

In an exemplary embodiment, portions of the bevel 128 along opposing sides of each of the rounded tabs 118 are symmetrical to one another (relative to the mid-point 132). The angle of the bevel 128 may also vary therealong, from the proximal-most point 132 to the distal end 122 thereof. In an exemplary embodiment, an angle of the bevel 128 may be greatest midway between the proximal-most point 132 and the distal end 122 of the rounded tab 118. It will be understood by those of skill in the art that a cross-sectional area of the interior surface 136 along each of the rounded tabs 118 will be smaller than a cross-sectional area of the of the exterior surface 134 along each of the rounded tabs 118.

The partial bevel 138 of each of the indentations 124 corresponds to the partial bevel 128 of the links 102 so that the rounded tabs 118 and indentations 124 or the adjacent links 102*a*, 102*b* movably engage one another. In particular, the partial bevel 138 of each of the indentations 124 is configured so that, the rounded tabs 118 and the indentations 124 of the proximal and distal engaging features 104, 106 mate with one another while permitting each rounded tab 118 to be rotated within the corresponding indentation 124, within a predetermined range of angulation.

According to one exemplary embodiment, partial bevels 128, 138 may extend at an angle of less than 10 degrees relative to an axis extending perpendicular to the exterior surface 134. In another exemplary embodiment, the partial bevels 128, 138 may extend at angles ranging from between, for example, 6 degrees and 9 degrees. It will be understood by those of skill in the art, however, that the bevels 128, 138 relative to the axis perpendicular to the exterior surface 134 of the articulating joint 100 may have any of a variety of angulations so long as the angle of the bevels 128, 138 of the diametrically opposing rounded tabs 118 and indentations 124 prevent the disengagement of adjacent links 102 of the articulating joint 100.

According to an exemplary embodiment, a proximal-most point 142 (e.g., midpoint) of each of the indentations includes a straight edge. In particular, a portion that is midway along an edge 140 or surface defining each indentation 124 extends perpendicular relative to the exterior surface 134 and the interior surface 136 of the link 102, while the bevel 138 extends along the edge 140 between the proximal-most point 142 and the distal edge 126 of the link 102, along opposing sides of the indentation 124, as shown in FIGS. 4 and 5. Since the proximal and distal engaging features 104, 106 are configured to mate with one another, similarly to the bevel 128 of the rounded tab 118, the portions of the bevel 138 extending along opposing sides of each of the indentations 124 in this embodiment are symmetrical to one another (relative to the midpoint).

In addition, similarly to the bevel 128, with which an angle of the bevel 138 corresponds, the angle of the bevel 138 may vary along the bevel 138, from the proximal-most point 142 to a distal end of the distal edge 126 thereof. In an exemplary embodiment, an angle of the bevel 138 is greatest midway between the proximal-most point 142 and the distal end of the distal edge 126 of the indentation 124.

In an exemplary embodiment, the links 102 of the articulating joint 100, including the angle of the beveled surfaces, are also symmetrical with respect to the plane along within which the links 102 may be rotated relative to one another. In other words, each of the rounded tabs 118 is symmetrical with respect to the plane of angulation in relation to the corresponding indentations 124 of the link with which it forms a hinge. Thus, the partial bevels 128, 138 extending along opposing sides of the rounded tabs 118 and the indentations 124, respectively, are sufficient to prevent adjacent ones of the links 102 from separating from one another while permitting relative movement—i.e., rotation—therebetween.

It will be understood by those of skill in the art that each of the links 102 may also be configured to include a plurality of slots 144 extending from the exterior surface 134 to the exterior surface 136, through a wall 146 thereof, where the slots 144 are configured to accommodate a wire, cable, or other control element therethrough. In an exemplary embodiment, the slots 144 of each of the links 102 extend through a portion of the wall 146 extending between the diametrically opposed distal engaging features 106 (and the proximal engaging features 104) of the link 102. For example, in one embodiment, the slots 144 are offset by 90 degrees about the longitudinal axis L, from the proximal and distal engaging features 104, 106 of the link 102. According to an exemplary embodiment, a portion of the wall extending between adjacent slots 144 along the longitudinal axis L are crimped radially inward so that a control element may be threaded through the inwardly crimped portions of each of the links 102 to facilitate bending and/or deflection of the articulating joint 100, as will be understood by those of skill in the art.

It will also be understood by those of skill in the art, that a proximal-most one of the links 102 will include only the distal engaging features 106 while a distal-most one of the links 102 will include only the proximal engaging features 104. In addition, although the exemplary embodiments show and describe the rounded tabs 118 as the proximal engaging feature 104 and the indentations 124 as the distal engaging feature 106, it will be understood by those of skill in the art that the exemplary articulating joint 100 may be oriented in either direction relative to a shaft of a medical device. In other words, in another embodiment, the rounded tabs 118 may extend from the distal end 110 while the correspondingly sized and shaped indentations 124 may be formed at the proximal end 108 of each of the links 102.

Figure 9:
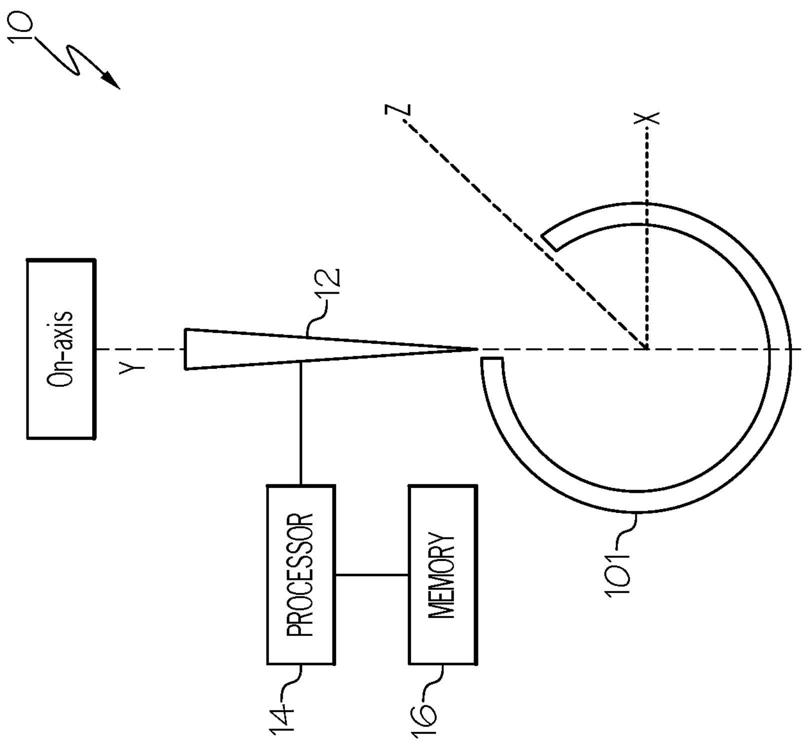
FIG. 9 shows a schematic drawing of a laser cutting system for lase cutting a tubular member according to the exemplary embodiment of FIG. 1.

According to an exemplary system and method for manufacturing the articulating joint 100, the links 102 thereof may be cut from a single, tubular member 101 using a 4-axis laser cutting system 10 including a laser 12 controlled via a processor 14 such to move a laser 12 along three axes while the tubular member 101 is rotated about the longitudinal axis L thereof (i.e., a fourth axis of movement). The laser cutting system 10 may include, for example, a picosecond laser or a femtosecond laser, with the laser 12 extending along one of the three axes (X, Y, Z) along which it is movable, as shown in FIG. 9, relative to the tubular member 101. According to an exemplary embodiment, the X-axis corresponds to an offset or distance of the laser 12 from the longitudinal axis L of the tubular member 101, the Y-axis corresponds to a distance of the laser 12 from the tubular member 101, and the Z-axis corresponds to the longitudinal axis L of the tubular member 101 about which the tubular member 101 is rotatable.

The processor 14 of one embodiment includes and/or is connected to a memory 16 configured to include instructions for laser cutting of the tubular member 101, as will be described in further detail below. The memory 16 may, for example, be a non-transitory computer-readable storage medium including instructions that are executable via the processor 14. The processor 14 may be configured to execute computer-executable instructions for operations from applications stored in the memory 16, to provide functionalities to the laser cutting system 10. It will be understood by those of skill in the art that although the laser cutting system 10 is shown as including a single processor 14 and a separate memory 16, the functionalities described with respect to the laser 12 may be achievable via a modular component connected to the processor 14 or via more than one processor 14. For example, the laser cutting system 10 may be comprised of a network of computing systems, each of which includes one or more of the components described above.

As described above, in an exemplary method of manufacture, the tubular member 101 is laser cut to define each of the links 102 by moving the laser 12 along the X, Y, Z axes while rotating the tubular member 101 about the longitudinal axis L (e.g., Z-axis). In particular, portions of the tubular member 101 are cut out to define the proximal and distal edges 120, 126 of each of the links 102. While the proximal-most ends 132, 142 of the rounded tabs 118 and indentations 124, respectively, are cut when the laser 12 is positioned substantially perpendicularly to the exterior surface 134 in alignment with the longitudinal axis L, the partial bevels 128, 138 of the rounded tabs 118 and indentations 124, respectively, are formed via a laser cut 114 extending through the wall 146 of the tubular member 101 at an angle relative to an axis perpendicular to the exterior surface 134 at that point.

Figure 7:
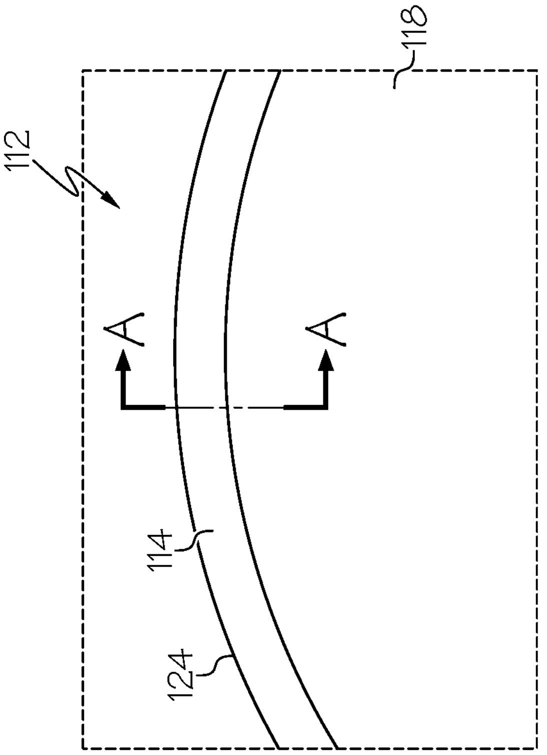
FIG. 7 shows an enlarged view of a cut formed between mating portions of the hinge between adjacent links of the articulating joint according to FIG. 6.
Figure 6:
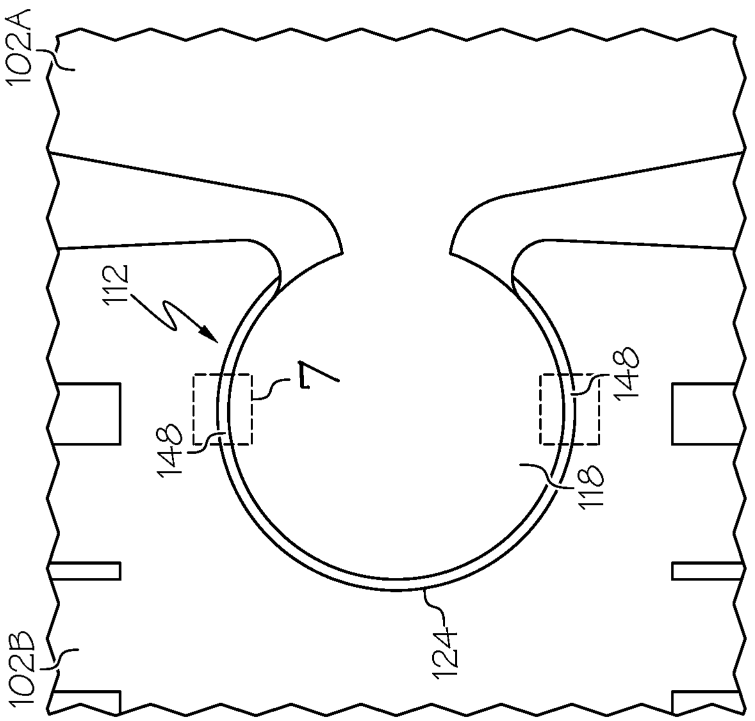
FIG. 6 shows an enlarged longitudinal side view of a hinge between adjacent links of the articulating joint according to FIG. 1.
Figure 8:
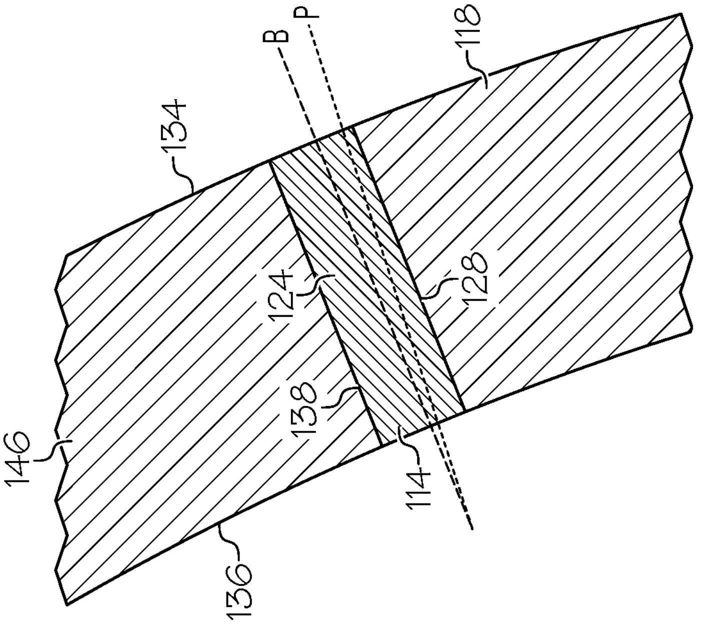
FIG. 8 shows a cross-sectional side view of the hinge along line A-A, according to FIG. 7.

As shown in FIGS. 6-8, the laser cut 114 along opposing sides 148 of the hinge 112 (e.g., portions of laser cut 114 extending between the proximal-most point 132 and the distal end 122 of the rounded tabs 118) is achieved by moving the laser 12 along the X-axis while also rotating the tubular member 101 about the longitudinal axis L and moving the laser 12 along the Z-axis. In particular, an angle of the laser cut 114 along the opposing sides 148 of the hinge 112 will be determined via an offset of the laser 12 relative to the longitudinal axis L and a rotation of the tubular member 101 about the longitudinal axis L.

It will be understood by those of skill in the art that an axis B along which the laser cut 114 extends through the tubular member 101 to define the bevels 128, 138 will have the greatest angle relative to an axis P, which is perpendicular to the exterior and the interior surfaces 134, 136 at that point, at a radially outer most point of the rounded tabs 118 and indentations 124. As discussed above, the axis B along which the laser cut 114 is formed may, in one embodiment, extend at an angle of less than 10 degrees relative to the axis P and, in another more specific embodiment, may extend at an angle ranging from between 6 and 9 degrees. It will be understood by those of skill in the art, however, that the angle of the axis B relative to the axis P may be varied, as desired, so long as the partial bevels 128, 138 defined via the laser cut 114 prevents adjacent links 102 of the articulating joint 100 from disengaging and/or being separated from one another while also permitting the adjacent links 102 to be rotated relative to one another, as described above.

The laser cut 114 is angled along the opposing sides 148 of the hinge 112 so that, when viewed from a side of the articulating joint, as shown in FIGS. 7-8, a point at which the bevels 128, 138 meet the interior surface 136 of the link 102 is not visible from an exterior of the articulating joint 100. As described above, the tubular member 101 is symmetrically cut about the longitudinal axis L and, in particular, about the plane along which the adjacent links 102*a*, 102*b* are rotatable, so that the partial bevels 128, 138 of the proximal and distal engaging features 104, 106, respectively, prevent the adjacent links 102*a*, 102*b* from separating from one another while also permitting the rounded tabs 118 of each of the links 102 to be rotated within the corresponding indentations 124 of an adjacent one of the links 102.

It will be appreciated by those skilled in the art that changes may be made to the embodiments described above without departing from the inventive concept thereof. It should further be appreciated that structural features and methods associated with one of the embodiments can be incorporated into other embodiments. It is understood, therefore, that this invention is not limited to the particular embodiment disclosed, but rather, modifications are also covered within the scope of the present invention as defined by the appended claims.

What is claimed is:

1. A method for manufacturing an articulating joint of a medical device, comprising:

laser cutting a tubular member to form the articulating joint including a plurality of links using a four-axis laser cutter including a laser movable along three axes and the tubular member rotatable about a longitudinal axis thereof, wherein each of the links extends from a proximal end to a distal end, the proximal end of each of the plurality of links including a proximal engaging feature and the distal end of each of the plurality of links including a distal engaging feature, the proximal engaging feature of one of the links configured to movably engage the distal engaging feature of an adjacent one of the links to form a hinge via which adjacent links are rotatable relative to one another and the articulating joint is movable between a straight configuration and a bent configuration, the proximal and distal engaging features including partial bevels corresponding to one another and extending therealong to prevent adjacent links from separating from one another, wherein the proximal engaging feature comprises a pair of rounded tabs, and the distal engaging feature comprises a pair of rounded indentions, and wherein the pair of rounded tabs of each link lies within a same plane as the pair of rounded tabs of each adjacent link in the straight configuration.

2. The method of claim 1, wherein the laser cuts the tubular member to define the hinge between adjacent links, wherein the pair of rounded tabs extends from diametrically opposing portions of a proximal edge of each of the plurality of links, and wherein the pair of rounded indentations extends through a wall of each of the plurality of links along a distal edge thereof.

3. The method of claim 2, wherein the laser cuts a bevel along opposing sides of each rounded tab of the pair of rounded tabs and each rounded indentation of the pair of rounded indentations, an angle of the bevel determined via a distance of the laser from a longitudinal axis of the tubular member and a rotation of the tubular member.

4. The method of claim 2, wherein the laser cuts out portions of the tubular member to define the proximal and distal edges of each of the links so that the proximal edge of each of the links tapers toward the pair of rounded tabs and the distal edge of each of the links tapers toward the pair of indentations so that there is sufficient space between adjacent links for the adjacent links to be rotated relative to one another.

5. The method of claim 1, wherein the laser extends perpendicular relative to the longitudinal axis along a portion of the tubular member to cut a straight edge along corresponding portions of the proximal and distal engaging features.

* * * * *